(12) United States Patent
Abe

(10) Patent No.: US 7,439,503 B2
(45) Date of Patent: Oct. 21, 2008

(54) CHARGED PARTICLE BEAM IRRADIATION METHOD, METHOD OF MANUFACTURING SEMICONDUCTOR DEVICE AND CHARGED PARTICLE BEAM APPARATUS

(75) Inventor: Hideaki Abe, Kanagawa (JP)

(73) Assignee: Kabushiki Kaisha Toshiba, Tokyo (JP)

(*) Notice: Subject to any disclaimer, the term of this patent is extended or adjusted under 35 U.S.C. 154(b) by 61 days.

(21) Appl. No.: 10/959,499

(22) Filed: Oct. 7, 2004

(65) Prior Publication Data
US 2005/0121610 A1    Jun. 9, 2005

(30) Foreign Application Priority Data
Oct. 8, 2003    (JP)    ............... 2003-349460

(51) Int. Cl.
*H01J 37/28* (2006.01)
(52) U.S. Cl. ............... 250/310; 250/492.22; 382/149
(58) Field of Classification Search ................ 250/310
See application file for complete search history.

(56) References Cited

U.S. PATENT DOCUMENTS 5,818,217 A    10/1998    Komatsu et al.
6,573,889 B1 *    6/2003    Georgiev .................. 345/419
6,868,175 B1 *    3/2005    Yamamoto et al. ........ 382/145
2005/0146714 A1 *    7/2005    Kitamura et al. ......... 356/237.2

FOREIGN PATENT DOCUMENTS

JP    5-151921    6/1993

OTHER PUBLICATIONS

Hideaki Abe, "Charged Particle Beam Apparatus, Charged Particle Beam Irradiation Method, and Method of Manufacturing Semiconductor Device", U.S. Appl. No. 10/742,998, filed Dec. 23, 2003.

* cited by examiner

*Primary Examiner*—David A. Vanore
*Assistant Examiner*—Phillip A. Johnston
(74) *Attorney, Agent, or Firm*—Finnegan, Henderson, Farabow, Garrett & Dunner, L.L.P.

(57) ABSTRACT

A charged particle beam irradiation method includes: obtaining shape information of an edge of a pattern to be inspected that is formed on a subject; creating a first line group substantially perpendicular to the pattern edge; creating a second line group substantially parallel with the pattern edge; specifying areas defined by the first line group and the second line group as a lattice group including irradiation positions of a charged particle beam; deciding an order to irradiate the areas with the charged particle beam so that the lattice group is sequentially scanned in a direction of the first or second line group; and scanning the subject with the charged particle beam in accordance with the irradiation order.

15 Claims, 9 Drawing Sheets

LINE PROFILE
OF A0-A1

LINE PROFILE
OF B0-B1

LINE PROFILE
OF C0-C1

LINE PROFILE
OF D0-D1

LINE PROFILE
OF E0-E1

LINE PROFILE
OF F0-F1

CHARGED PARTICLE BEAM IRRADIATION METHOD, METHOD OF MANUFACTURING SEMICONDUCTOR DEVICE AND CHARGED PARTICLE BEAM APPARATUS

CROSS REFERENCE TO RELATED APPLICATION

This application claims benefit of priority under 35USC §119 to Japanese Patent Application No. 2003-349460, filed on Oct. 8, 2003, the contents of which are incorporated by reference herein.

BACKGROUND OF THE INVENTION

1. Field of the Invention

The present invention relates to a charged particle beam irradiation method, a method of manufacturing a semiconductor device and a charged particle beam apparatus, and is directed to, for example, specifying of an electron beam irradiation position in scanning with an electron beam.

2. Related Background Art

For observing a subject by use of a charged particle beam apparatus, for example, a scanning electron microscope (SEM), raster scanning is performed with an electron beam emitted from an electron gun through a scanning deflector to detect secondary electrons, reflected electrons and back scattering electrons (hereinafter referred to as secondary electrons and the like) produced from the surface of the subject due to electron beam irradiation, and an obtained signal is then processed to acquire an image (SEM image) based on the electron beam irradiation. The raster scanning is characterized in that the position for irradiation of the electron beam continuously moves, for example, from left to right in a screen. In accordance with image display that has heretofore been generally used, a secondary electron signal acquired at a scanning position on the subject is transmitted to elements (pixels) for image display to display a two-dimensional image. The elements for image display are generally arranged equally in horizontal and vertical directions, and in the raster scanning, horizontal scanning is followed by vertical scanning, and the horizontal scanning is again performed, which operation is repeated, as shown in FIG. 8A.

However, when irregular shapes such as an LSI pattern or parts of different materials are scanned with the electron beam, charges may be increased depending on the shape of the pattern and the scanning direction of the electron beam, thus causing contrast variance in the SEM image. Moreover, between an edge perpendicular to the scanning direction of the electron beam and an edge parallel with the scanning direction, a difference may be made in contrast and image resolution at an edge portion. This is apparent from line profiles representing grayscale values of the edge portions. For example, in the scanning along a D0-D1 direction perpendicular to a pattern edge EP1 in FIG. 8A, its line profile indicates a sharp rise in contrast as shown in FIG. 8C, while in the scanning along a C0-C1 direction slanted with respect to the pattern edge EP1, its line profile indicates a gentle rise as shown in FIG. 8B.

Thus, a difference is made in the resolution of the pattern edges depending on the scanning direction even with the same sectional shape. In LSI patterns such as simple line patterns that have been conventionally measured, there has not been a specific problem with the resolution of the edge portions because an image is obtained in a scanning direction perpendicular to a longitudinal direction of the pattern. However, along with the miniaturization and complication in the recent LSI patterns, one-dimensional measurement of the LSI patterns and the like alone does not enable adequate evaluation of shapes and process management in addition to a stronger tendency to make two-dimensional shape evaluation by use of the two-dimensional image obtained by the raster scanning. Items in this shape evaluation includes, for example, the area and circumferential length of a hole pattern and the degree of roundness at pattern corners, as well as the conventional line width of the line pattern.

As described above, the raster scanning might cause the contrast variance depending on the pattern shape and the scanning direction and changes in resolution due to the direction of the edge. Therefore, the two-dimensional shape evaluation is implemented from the image obtained by the raster scanning, a measurement result may include the influence of the scanning direction, in which case an accurate measurement result can not be obtained. Thus, a scanning technique other than the raster scanning is required in order to obtain an image without the influence of the scanning direction.

One of the scanning techniques without the influence of the scanning direction is random scanning (e.g., Japanese Patent Publication Laid-open No. 5-151921). One characteristic of this technique is that irradiation position information signals which specify an electron beam irradiation position in a scanning plane to be scanned with the electron beam are sequentially output so that each of them randomly specifies the irradiation position, and the electron beam is applied to the irradiation positions corresponding to the output irradiation position information signals.

However, if the whole irradiation area for the electron beam corresponding to measurement magnification is randomly scanned, there is a problem that a significant amount of time is needed to obtain an image for measurement.

Furthermore, the problem of scanning perpendicularly to the pattern edge is that, because the elements for image display are arranged equally in horizontal/vertical directions in the ordinary image display, if scanning is performed with the electron beam in an oblique direction E0-E1 to indicate an image signal as shown in FIG. 9A, its line profile indicates a sharp rise as shown in FIG. 9B, but lattices in the oblique direction do not link together to cause a lack of information in the image signal.

Still further, in order to measure the hole patterns, such a technique has also been put into practical use wherein scanning is performed with the electron beam in a diametric direction of the hole and the measurement is performed after conversion into a polar coordinate system. However, the polar coordinate system is a technique which is applicable only to the hole patterns and not applicable to an arbitrary pattern shape.

BRIEF SUMMARY OF THE INVENTION

According to a first aspect of the present invention, there is provided a charged particle beam irradiation method comprising:

obtaining shape information of an edge of a pattern to be inspected that is formed on a subject;

creating a first line group substantially perpendicular to the pattern edge;

creating a second line group substantially parallel with the pattern edge;

specifying areas defined by said first line group and said second line group as a lattice group including irradiation positions of a charged particle beam;

deciding an order to irradiate the areas with the charged particle beam so that the lattice group is sequentially scanned in a direction of the first or second line group; and scanning the subject with the charged particle beam in accordance with the irradiation order.

According to a second aspect of the present invention, there is provided a charged particle beam irradiation method comprising:

scanning a subject on which a pattern to be inspected is formed along a plurality of directions crossing an edge of the pattern;

obtaining signal waveforms from signals obtained by the scanning in a manner to correspond to the plurality of directions, respectively;

calculating a spatial frequency with respect to each of the signal waveforms;

specifying a direction in which the spatial frequency becomes the highest as a suitable scanning direction; and scanning again the subject with a charged particle beam along the specified scanning direction.

According to a third aspect of the present invention, there is provided a method of manufacturing a semiconductor device comprising a charged particle beam irradiation method including:

obtaining shape information of an edge of a pattern to be inspected that is formed on a subject;

creating a first line group substantially perpendicular to the pattern edge;

creating a second line group substantially parallel with the pattern edge;

specifying areas defined by said first line group and said second line group as a lattice group including irradiation positions of a charged particle beam;

deciding an order to irradiate the areas with the charged particle beam so that the lattice group is sequentially scanned in a direction of the first or second line group; and scanning the subject with the charged particle beam in accordance with the irradiation order.

According to a fourth aspect of the present invention, there is provided a method of manufacturing a semiconductor device comprising a charged particle beam irradiation method including:

scanning a subject on which a pattern to be inspected is formed along a plurality of directions crossing an edge of the pattern;

obtaining signal waveforms from signals obtained by the scanning in a manner to correspond to the plurality of directions, respectively;

calculating a spatial frequency with respect to each of the signal waveforms;

specifying a direction in which the spatial frequency becomes the highest as a suitable scanning direction; and scanning again the subject with a charged particle beam along the specified scanning direction.

According to a fifth aspect of the present invention, there is provided a charged particle beam apparatus comprising:

a charged particle beam source section which generates a charged particle beam and irradiates a subject with the charged particle beam, a pattern to be inspected being formed on the subject;

a deflector which deflects the charged particle beam to scan the subject therewith;

a calculator which creates a first line group substantially perpendicular to the pattern edge and a second line group substantially parallel with the pattern edge from shape information of an edge of the pattern to specify one of directions of the first and second line groups as a scanning direction and which specifies areas defined by said first line group and said second line group as a lattice group including irradiation positions of the charged particle beam, respectively and which decides irradiation positions and an irradiation order of the charged particle beam so that the areas of the subject corresponding to said specified areas are sequentially scanned in the scanning direction; and a deflection controller which controls the deflector so that the irradiation positions are sequentially irradiated with the charged particle beam in the irradiation order.

According to a sixth aspect of the present invention, there is provided a charged particle beam apparatus comprising:

a charged particle beam source which generates a charged particle beam and irradiates a subject with the charged particle beam, a pattern to be inspected being formed on the subject;

a deflector which deflects the charged particle beam to scan the subject therewith;

a calculator which receives waveform information of a signal obtained by scanning the subject with the charged particle beam along a plurality of directions crossing an edge of the pattern to be inspected to calculate a spatial frequency of the signal waveform and which specifies a direction in which the spatial frequency becomes the highest among the plurality of directions as a suitable scanning direction; and a deflection controller which controls the deflector so that the subject is scanned with the charged particle beam along the scanning direction specified by the calculator.

DETAILED DESCRIPTION OF THE INVENTION

Some embodiments of the present invention will hereinafter be described in reference to FIGS. 1A to 7. It is to be noted that an electron beam is used as a charged particle beam in the following embodiments which will be described, but the present invention is not limited thereto, and can naturally be applied when, for example, an ion beam is used as the charged particle beam.

(1) First Embodiment of Charged Particle Beam Irradiation Method

Figure 1A:
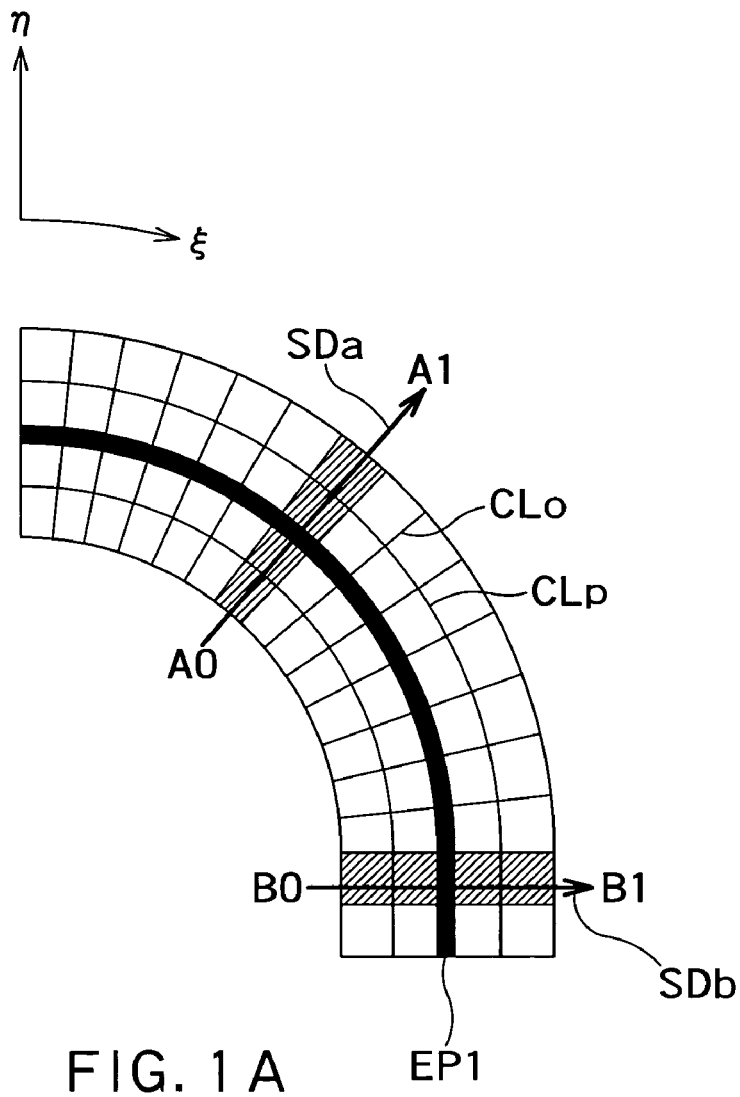
FIGS. 1A to 1C are diagrams explaining the outline of a first embodiment of a charged particle beam irradiation method according to the present invention.
Figure 1B:
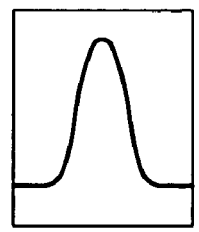
Figure 1C:
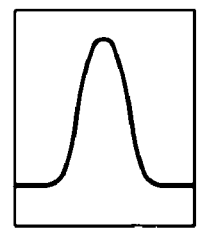

FIGS. 1A to 1C are diagrams explaining the outline of a first embodiment of a charged particle beam irradiation method according to the present invention. As shown in FIG. 1A, in an electron beam irradiation method of the present embodiment, a curve group CLo perpendicular to a pattern edge EP1 and a curve group CLp parallel with the pattern edge EP1 are formed, and a lattice group defined by these curve groups CLo and CLp is set as an irradiation area for the electron beam. Further, a scanning position thus set is scanned with the electron beam in a direction (direction of the curve group CLo) perpendicular to the pattern edge EP1 (in scanning directions SDa, SDb in an example shown in FIG. 1A). A coordinate system of FIG. 1A is expressed by a system ($\xi$-$\eta$ coordinate system) which is converted from an ordinary horizontal/vertical coordinate system (x-y coordinate system), and scanning directions A0-A1 and B0-B1 are both in a $\eta$ direction, and scanning is performed with the electron beam in the $\eta$ direction such that an SEM image is formed in the $\xi$-$\eta$ coordinate system.

With regard to an irradiation position for the electron beam, centric coordinates of a lattice defined by first and second curve groups are calculated by the x-y coordinate system, and a deflector of the electron beam is controlled so that the irradiation of the electron beam is directed to this irradiation position. A secondary electron signal generated by the irradiation of the electron beam is detected by a detector (see a numeral 66 in FIG. 7) and amplified, and then stored in an image memory (see an edge perpendicular scanning image memory 24 in FIG. 7) of the $\xi$-$\eta$ coordinate system corresponding to the irradiation position. This is repeated in a direction perpendicular to the pattern edge EP1, that is, a $\eta$ direction, thereby enabling the scanning with the electron beam in the direction perpendicular to the pattern edge EP1.

Figure 2:
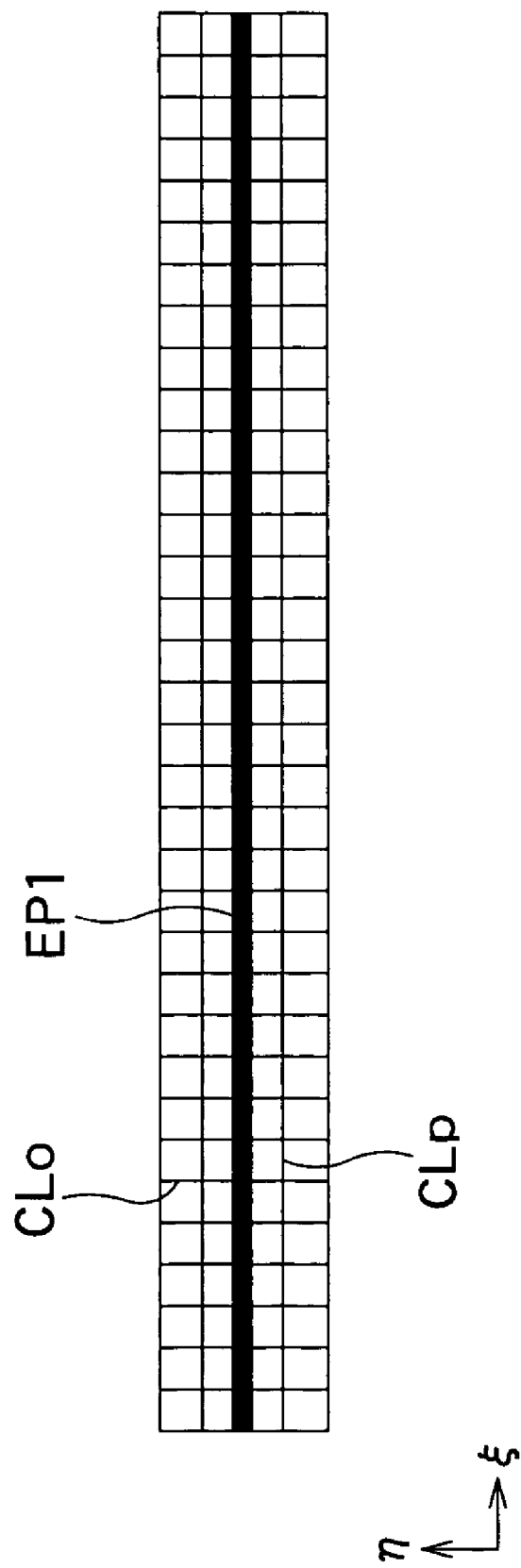
FIG. 2 is a diagram showing an example in which a scanning plane in the charged particle beam irradiation method shown in FIG. 1 is expressed by a $\xi$-$\eta$ coordinate system.

FIG. 2 shows an example in which such a scanning plane is expressed by the $\xi$-$\eta$ coordinate system. As can be seen, the pattern edge EP1 is one straight line, and a $\xi$ axis is in a direction horizontal with respect to the pattern edge EPl while a $\eta$ axis is in a direction perpendicular to the pattern edge EPl. Comparing line profiles in the scanning directions A0-A1 and B0-B1, similar sharp rises occur in contrast, and the same amount of information can be obtained without any lack of pixel information, as shown in FIGS. 1B and 1C, respectively.

Figure 3:
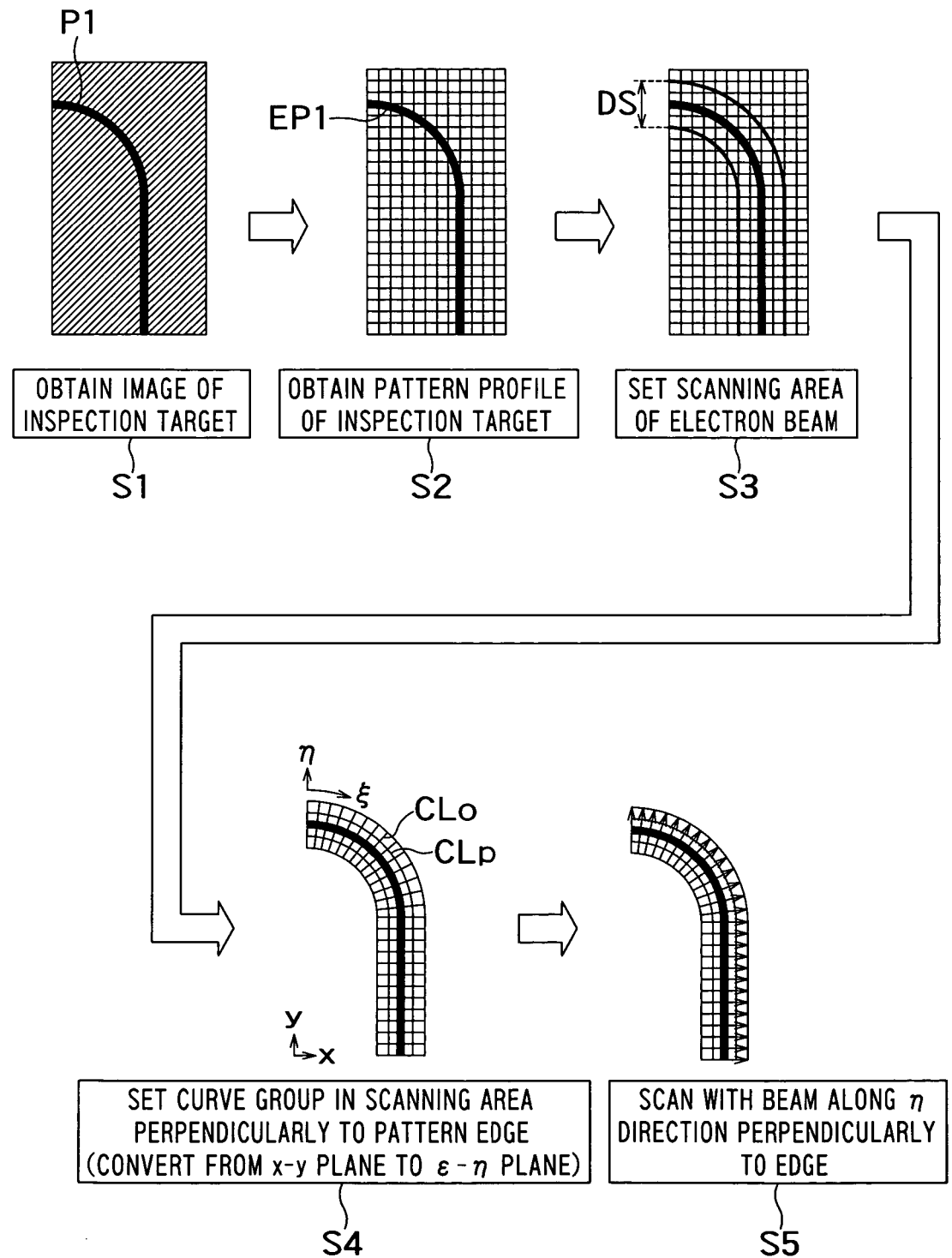
FIG. 3 is a flowchart explaining a specific procedure of the charged particle beam irradiation method shown in FIG. 1.

A more specific procedure for the beam irradiation method of the present embodiment will be described referring to a flowchart of FIG. 3.

First, a profile shape of a pattern to be inspected is obtained (step S1). The profile shape can also be obtained by use of the SEM image obtained by the actual raster scanning of a pattern to be inspected P1 with the electron beam, by use of design information and CAD information, and further by use of shape simulation information such as lithography. FIG. 3 shows a technique to actually perform the raster scan with the electron beam. At this stage, the scanning plane is expressed as the SEM image in the x-y coordinate system. This SEM image is used to extract the profile shape, that is, the pattern edge EP1 (step S2). The pattern edge EP1 can be extracted by, for example, digitizing process or image processing including Laplacian filters and Sobel filters. Various techniques can be utilized for the extraction of the profile itself.

Next, a distance for scanning with the electron beam perpendicularly to the pattern edge EP1 (hereinafter be referred to as a scanning distance) is set, and a scanning area is set (step S3). An area where the scanning distance passes along the pattern edge EP1 is the scanning area for the electron beam. Subsequently, as shown in FIG. 2, the scanning plane is converted from the x-y coordinate system to the $\xi$-$\eta$ coordinate system such that the curve group CLo perpendicular to the pattern edge EP1 and the curve group CLp parallel with the pattern edge in the set scanning area are specified (step S4). A specific technique to form such curve groups CLo and CLp will be described later.

After the lattice group is thus formed, scanning is performed with the electron beam along the $\eta$ axis of the $\xi$-$\eta$ coordinate system (step S5), thereby allowing the SEM image in the $\xi$-$\eta$ coordinate system to be obtained.

There are a number of techniques to form the curve group CLo perpendicular to the pattern edge and the curve group CLp parallel with the pattern edge and any of the techniques may be utilized. A geometric technique and a technique using an equipotential curve will be described below.

(A) Geometric Technique

Figure 4:
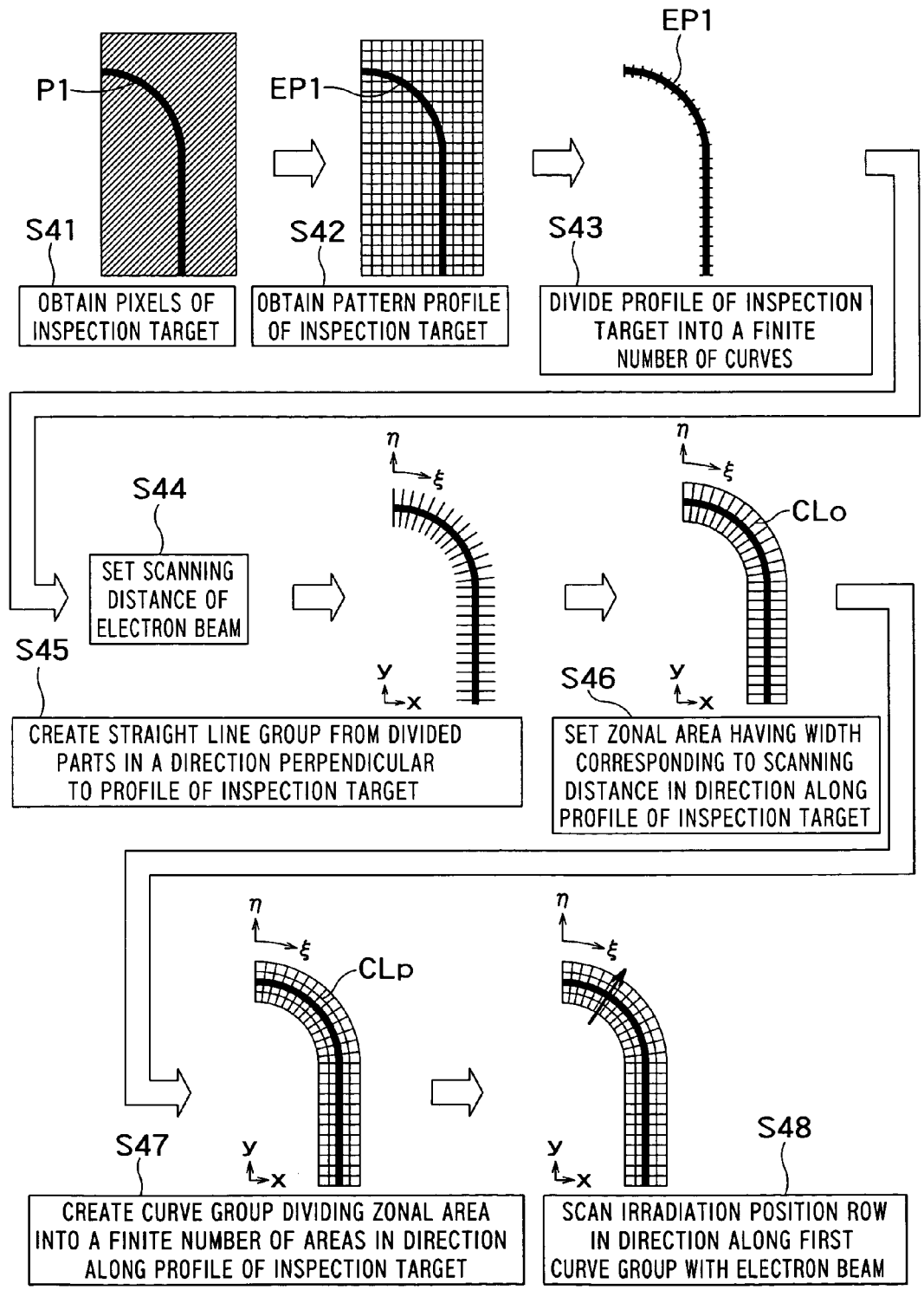
FIG. 4 is a flowchart explaining one example of a specific procedure of creating a curve group perpendicular to a pattern profile.

FIG. 4 is a flowchart explaining a technique to form the curve groups CLo and CLp using the geometric technique.

First, an SEM image of the pattern to be inspected P1 is obtained (step S41), and the profile shape EP1 of the pattern to be inspected P1 is extracted (step S42), and then the profile EP1 is divided into a finite number of curves (step S43). The number of divisions and division space are set in advance. Here, if the division space is set locally narrow, a part desired to be observed can be elaborately scanned. For example, as a part having a large curvature is susceptible to the influence of the scanning direction, the division space needs to be small. In that case, if an amount of angle change is calculated for a divided curve in relation to the adjacent curve, a change in its curvature can be confirmed. By setting this division space so as to correspond to the angle change, the number of divisions can be optimized.

Next, the scanning distance of the electron beam is set (step S44). Then, a curve group is created which has a length corresponding to the scanning distance in a direction perpendicular to the profile EP1 to be inspected from the parts where the profile EP1 to be inspected is divided into a finite number of curves (step S45). This curve group corresponds to the above-mentioned curve group CLo, and can be regarded as a straight line group when the scanning direction is short. The direction of the curve group CLo is perpendicular to the pattern edge, but this direction can be set by using the direction of a straight line (normal) perpendicular to a line (tangent to the profile EP1) passing a plurality of points adjacent to the profile EP1.

Subsequently, a zonal area is set which has a width corresponding to the scanning distance in a direction along the profile of the pattern to be inspected (step S46). Further, the curve group CLp is created which divides the zonal area into a finite number of areas in a direction along the inspection target (step S47). Preset values are used for the number of divisions and the division space, but the division space can be smaller in parts close to the profile.

In this way, the lattice group including lattice rows directed perpendicularly to the profile is formed from the curve group CLo perpendicular to the profile to be inspected and the curve group CLp along the profile. The lattice rows thus specified to be arranged in a direction crossing the profile EP1 ($\eta$ axis direction) are set as the scanning direction for the electron beam (step S48). Thus, the irradiation positions of the electron beam during scanning are continuously arranged in the scanning direction of the electron beam. When scanning in a direction perpendicular to the profile EP1, the scanning plane is scanned with the electron beam with the use of a deflector in an electronic optical system, to which a corresponding scanning signal is sent. It is to be noted that this scanning direction can also be set to a direction along the profile (ξ direction). In that case, scanning is performed with the electron beam on the lattice rows arranged in the direction along the profile (axis ξ direction). Signals generated from the inspection target by scanning with the electron beam are sequentially output in accordance with the lattice rows arranged in the scanning direction.

(B) Technique using Equipotential Curve

Figure 5:
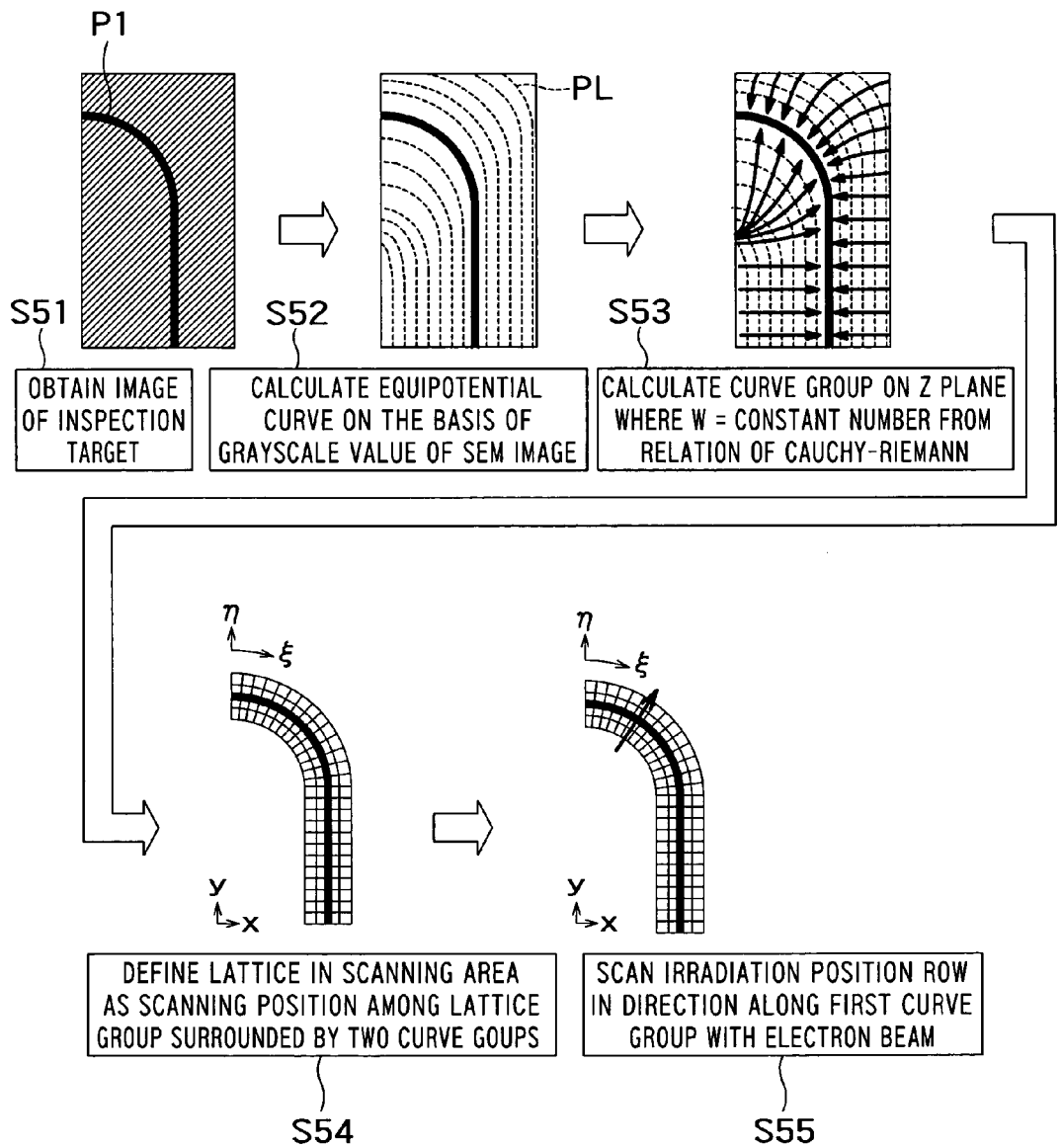
FIG. 5 is a flowchart explaining another example of a specific procedure of creating the curve group perpendicular to a pattern profile.

FIG. 5 is a flowchart explaining a method of forming the curve groups by use of the equipotential curve. To roughly explain this technique, the SEM image obtained by the raster scanning to extract the profile is used to draw an equipotential curve in accordance with grayscale values of this SEM image, and the scanning is performed with the electron beam along the curve group obtained by creating the curve group perpendicular to this equipotential curve.

First, an SEM image of the pattern to be inspected P1 is obtained by the raster scanning (step S51). Next, a plane of the SEM image is defined as a complex plane z=x+iy, and a potential function of the image at an arbitrary position zi on the image is defined as in the following equation on the basis of a grayscale value gi of a pixel at a position zi=xi+iyi on the complex plane.

$$V(z)=\Sigma\{f(gi)/h(|z-zi|)\} \quad \text{(Equation 1)}$$

wherein f (gi) is a monotone function with respect to gi, h (|z-zi|) is a function which decreases smoothly with |z-zi| and is a function differentiable on a z plane. Next, an equipotential curve of this function is calculated (step S52). The obtained equipotential curve is indicated in FIG. 5 by a broken line PL. This equipotential curve corresponds to the above-mentioned curve group CLp. Subsequently, a function W (z) derived from the relation of the following Cauchy-Riemann with the potential function in Equation 1 mentioned above is calculated.

$$\partial V/\partial x=\partial W/\partial y, \; \partial V/\partial y=-\partial W/\partial x \quad \text{(Equation 2)}$$

Furthermore, W is calculated by a numerical calculation, and curve groups on the z plane where W=constant number are sequentially created (step S53). The value of the constant number at this point can be adjusted to set the scanning distance. Because a function V+iW is a regular function, this curve group is always perpendicular to the equipotential curve by the principle of complex analysis. In other words, this curve group corresponds to the curve group CLo perpendicular to the above-mentioned pattern edge. Next, the scanning distance is set to define the scanning area for the electron beam (step S54), and the scanning is performed with the electron beam along the obtained curve group CLo (step S55), thereby enabling the scanning perpendicular to the pattern edge.

Thus, according to the present embodiment, scanning is performed with the charged particle beam in a direction perpendicular to or parallel with the pattern profile in an arbitrary shape, thereby making it possible to stably obtain highly accurate profile information without the influence of the scanning direction of the electron beam.

(2) Second Embodiment of Charged Particle Beam Irradiation Method

Next, a second embodiment of the charged particle beam irradiation method according to the present invention will be described. The present embodiment is concerned with a method of using the spatial resolution of the pattern edge to set a direction perpendicular to the profile.

Figure 6:
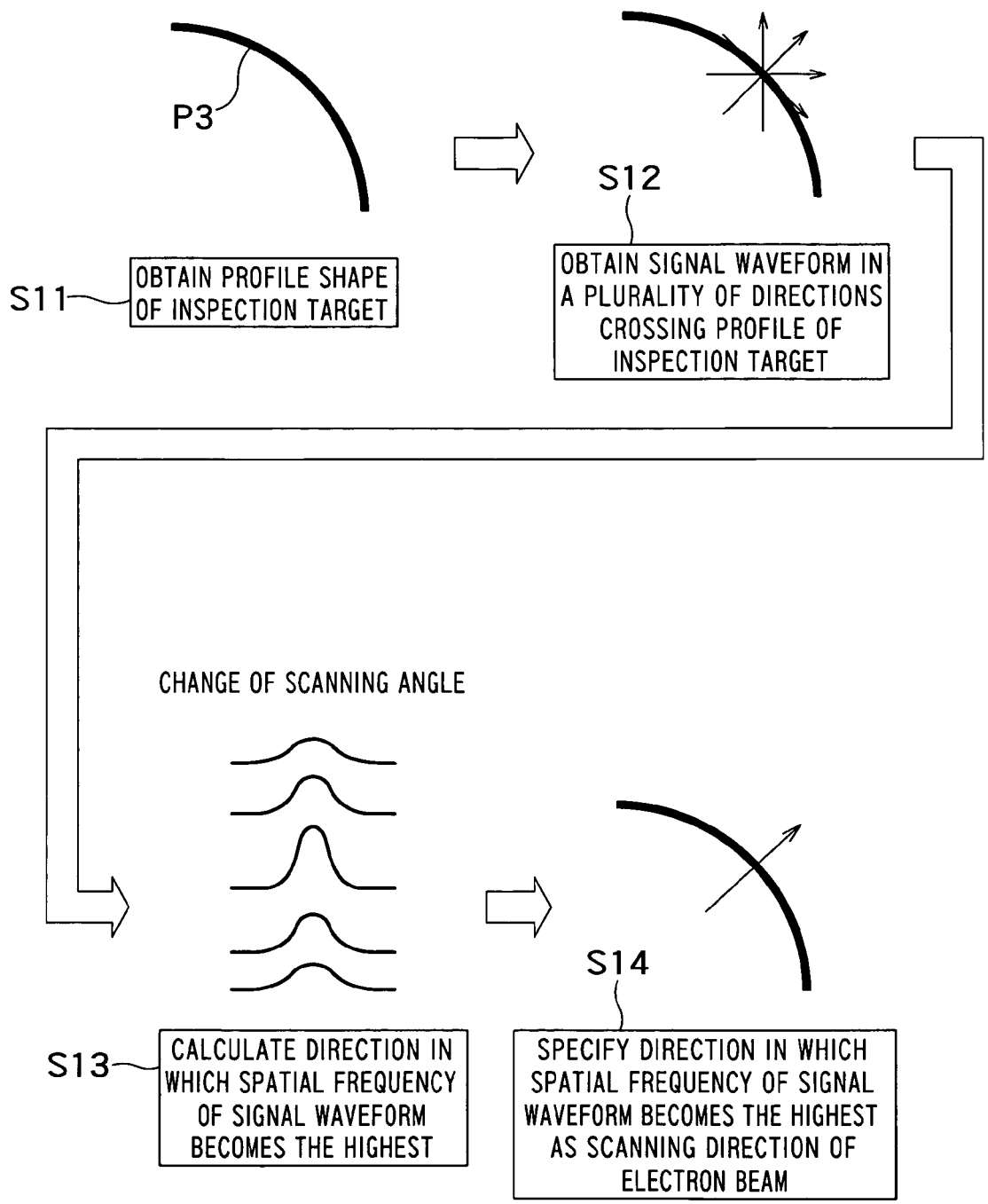
FIG. 6 is a flowchart explaining the outline of a second embodiment of the charged particle beam irradiation method according to the present invention.

FIG. 6 is a flowchart explaining the outline of the present embodiment. First, a profile shape of a pattern to be inspected P3 is obtained (step S11), and then signal waveforms of a plurality of search angles at a position on the profile of the obtained inspection image are obtained (step S12), so that, from a spatial frequency of the signal waveform in each search angle, the relation between the search angle and the spatial frequency is calculated. The spatial frequency of the signal waveform indicates a degree of signal intensity such as sharpness of rising signal in a waveform, which is represented by the spatial resolution of the pattern edge portion. The search angle of the signal waveform at which the spatial frequency becomes the highest is calculated from the relation between the search angle and the spatial frequency (step S13), and is set as a direction SD which is the most suitable for scanning with the electron beam (step S14). Here, in obtaining the signal waveforms in a plurality of directions, the angle at which the spatial frequency becomes the highest can be obtained not from a static image but by actually scanning with the electron beam in the plurality of directions.

Since the search angle of the signal waveform at which the spatial frequency becomes the highest is set as the most suitable scanning direction, highly accurate profile information can be stably obtained without the influence of the scanning direction of the electron beam.

(3) Method of Manufacturing Semiconductor Device

Using the above-described embodiments of the charged particle beam irradiation method, highly accurate profile information on the pattern can be stably obtained without the influence of the scanning direction of the charged particle beam, so that a semiconductor device can be manufactured with a high throughput and a high yield ratio.

(4) One Embodiment of Charged Particle Beam Apparatus

Figure 7:
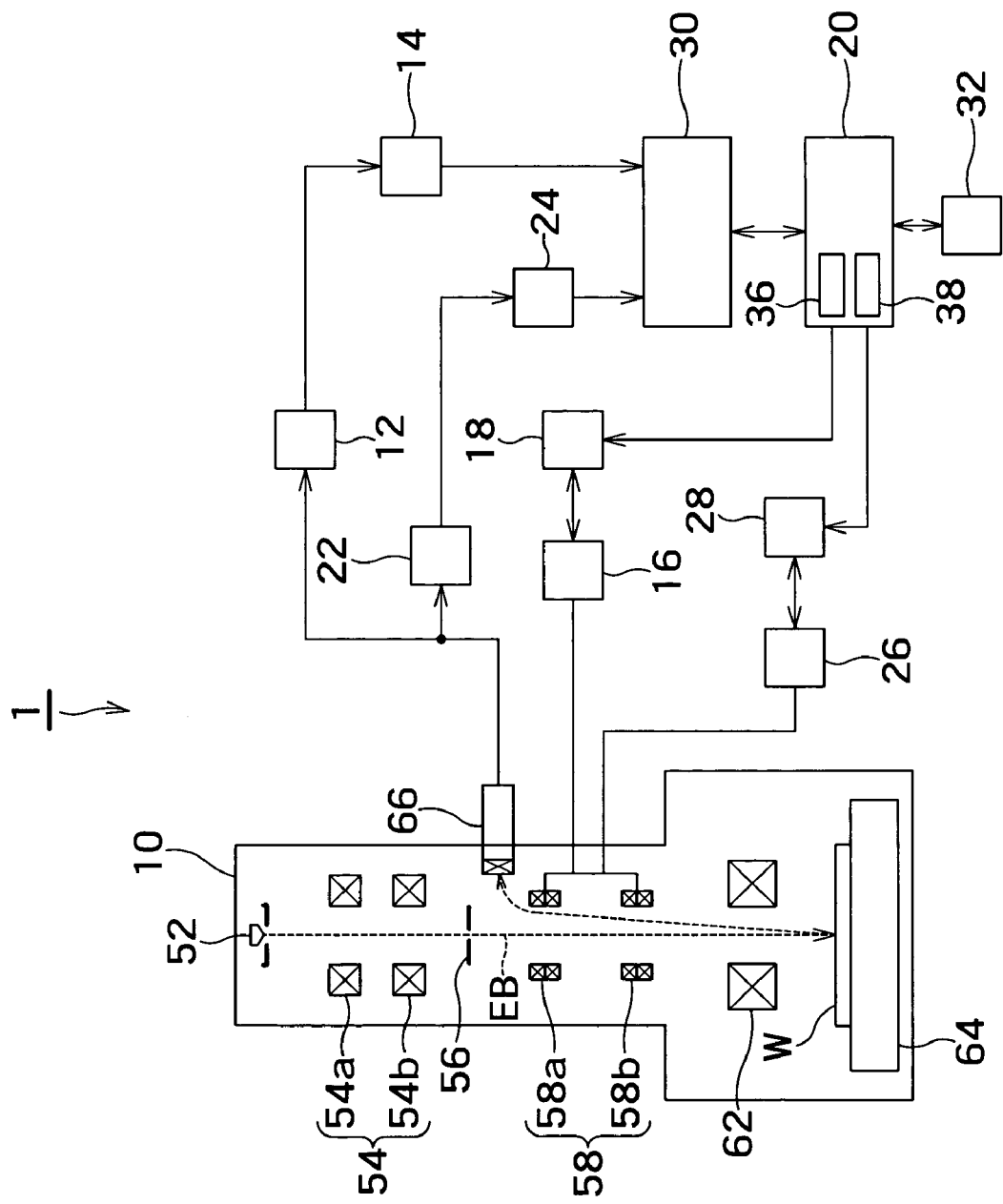
FIG. 7 is a block diagram showing a schematic configuration in one embodiment of a charged particle beam apparatus according to the present invention.
Figure 8A:
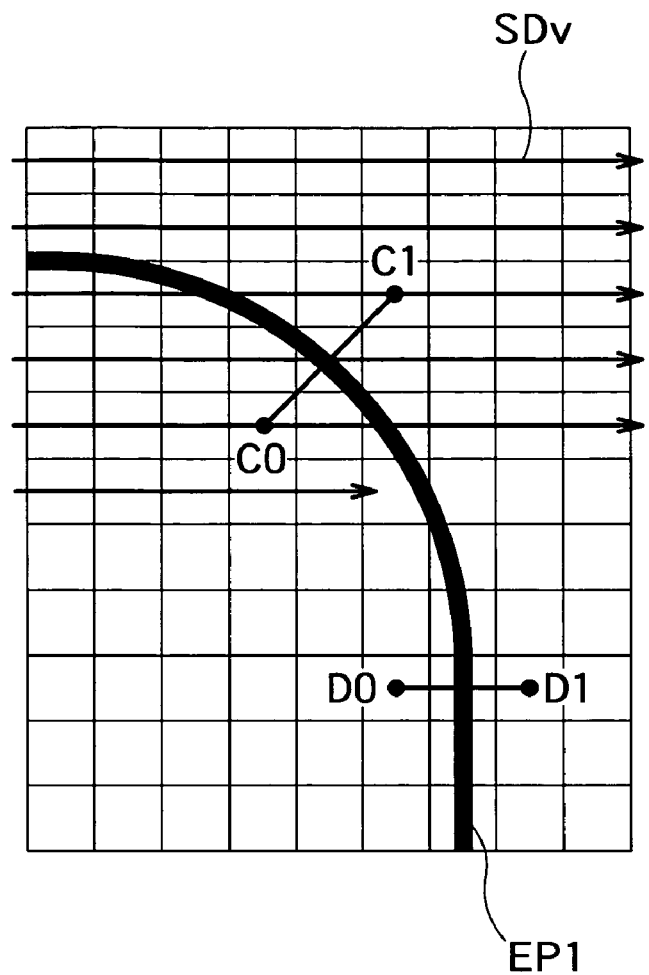
FIGS. 8A to 8C are diagrams explaining a method of performing a raster scan with an electron beam on a perpendicular lattice as one of the background arts relating to the invention of the present application.
Figure 8B:
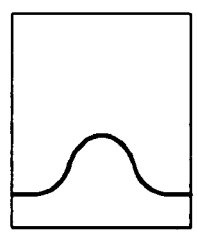
Figure 8C:
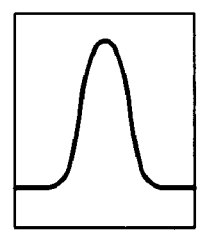
Figure 9A:
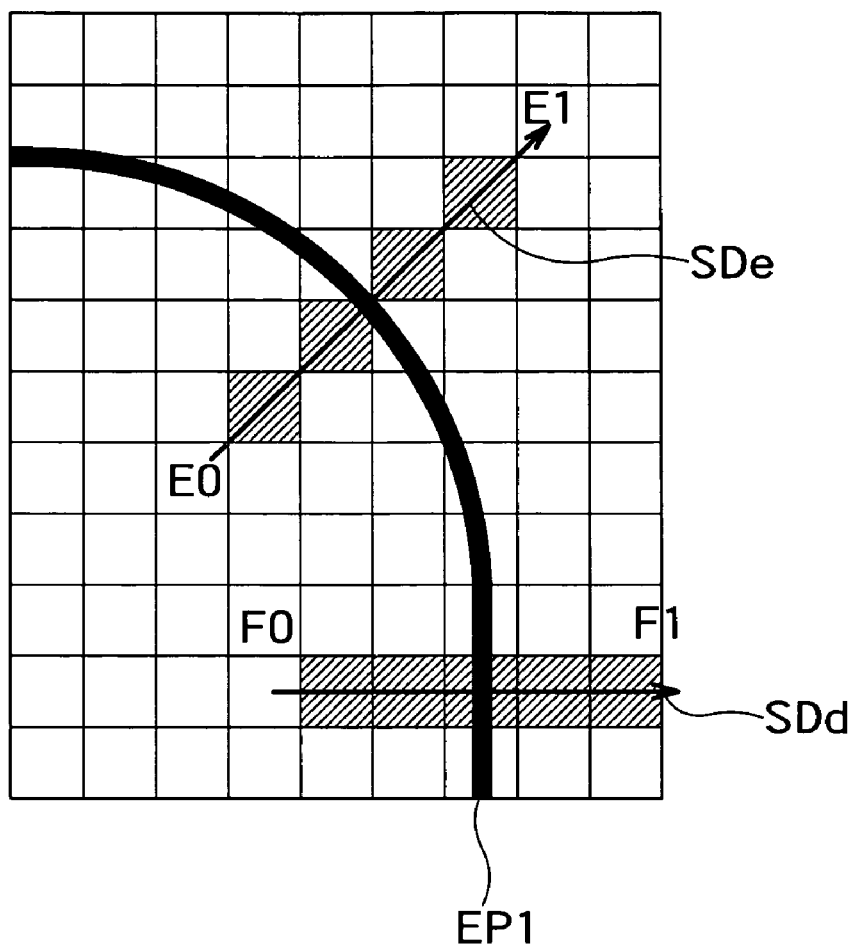
FIGS. 9A to 9C are diagrams explaining a method of obliquely scanning with the electron beam on the perpendicular lattice as one of the background arts relating to the invention of the present application.
Figure 9B:
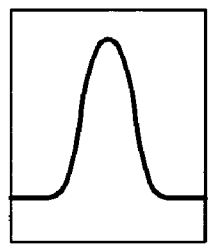
Figure 9C:
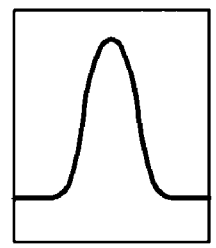

One embodiment of a charged particle beam apparatus according to the present invention will be described referring to FIG. 7. One example of the apparatus which implements the above-mentioned charged particle beam irradiation method is shown in a block diagram of FIG. 7. An electron beam apparatus 1 shown in FIG. 7 is characterized by comprising an electron beam irradiation section 10, a main computer 20, an image processing section 30 and a pattern edge position memory 32, in addition to a double-system deflection controller and image forming unit, and characterized in that the main computer 20 includes double-system calculators. Here, the double system represents a system of raster scanning and a system of edge perpendicular scanning for scanning perpendicularly to the pattern edge. The reason that these components are separated into the two systems is that the raster scanning is based on an orthogonal coordinate system, that is, the x-y coordinate system, and therefore allows the scanning position to be easily calculated, while the edge perpendicular scanning needs to get adapted to an arbitrary pattern shape, so that the number of dots at the scanning position and image memory capacity greatly vary depending on the shape of the pattern to be inspected.

The electron beam irradiation section 10 includes an electron gun 52, a condenser lens 54, an aperture 56, a scanning deflector 58, an objective lens 62, a stage 64 and a detector 66. The scanning deflector 58 has a horizontal scanning deflector 58a and a vertical scanning deflector 58b. A wafer W having a pattern to be observed or measured (not shown) formed on its upper surface is mounted on an upper surface of the stage 64. The electron gun 52 generates an electron beam EB, and this electron beam EB passes through the condenser lens 54, the aperture 56 and the objective lens 62 to reach the pattern on the upper surface of the wafer W where it is scanned by the scanning deflector 58. Secondary electrons and the like are produced from the surface of the wafer W due to the irradiation of the electron beam EB, and the secondary electrons and the like are detected by the detector 66, and signals dependent on their signal intensity are processed by the image forming unit of each system.

The main computer 20 includes a raster scanning calculator 36 and an edge perpendicular scanning calculator 38. The raster scanning calculator 36 calculates the irradiation position for the raster scanning. The edge perpendicular scanning calculator 38 calculates the direction perpendicular to the pattern edge and the irradiation position in accordance with at least one of the above-described embodiments of the charged particle beam irradiation method. As described above, the two scanning methods are totally different, so that deflection systems need to be completely independent. The deflection controller of the raster scanning system includes a raster scanning deflection controller 16 for the scanning deflector 58 to perform raster scanning, and a raster scanning controller 18 which generates a deflection signal for raster scanning and supplies the deflection signal to the raster scanning deflection controller 16. The deflection controller of the edge perpendicular scanning system includes an edge perpendicular scanning deflection controller 26 for the scanning deflector 58 to scan perpendicularly to the pattern edge, and an edge perpendicular scanning controller 28 which generates a scan signal for edge perpendicular scanning and supplies the scan signal to the edge perpendicular scanning deflection controller 26.

The image forming unit of the raster scanning system includes a raster scanning image converter 12 and a raster scanning image memory 14. The raster scanning image converter 12 converts a signal of the secondary electrons and the like detected by the detector 66 in the raster scanning into a two-dimensional image. The raster scanning image memory 14 stores the two-dimensional image obtained by the raster scanning. Similarly, an edge perpendicular scanning image converter 22 converts a signal of the secondary electrons and the like detected by the detector 66 in the edge perpendicular scanning into an image in accordance with the coordinate system ($\xi$-$\eta$ coordinate system) perpendicular to the edge, and the edge perpendicular scanning image memory 24 stores the image obtained by the edge perpendicular scanning. The image memory is also separated into the two systems because an ordinary two-dimensional image can be formed in the raster scanning, but the ordinary two-dimensional image can not be displayed in the edge perpendicular scanning and the image can be formed only in the orthogonal coordinate system.

According to the present embodiment, in addition to the system for the raster scanning, there are provided the calculator 38, the deflection controller and the image forming unit for the edge perpendicular scanning in which scanning is performed perpendicularly to the pattern edge, so that the highly accurate profile information can be stably obtained without the influence of the scanning direction of the electron beam.

While the embodiments of the present invention have been described above, the present invention is not limited to the above embodiments, but various modifications can naturally be applied within the scope thereof. For example, while the embodiment of the electron beam apparatus which comprises the two systems including the system of raster scanning and the system of edge perpendicular scanning has been described above, the electron beam apparatus may comprise a calculator, a deflection controller and an image forming unit for scanning in parallel with the pattern edge, instead of or in addition to the edge perpendicular scanning system.

What is claimed is:

1. A charged particle beam irradiation method comprising:
   obtaining shape information of an edge of a pattern to be inspected that is formed on a subject;
   creating, from the shape information, a first line group substantially perpendicular to the pattern edge;
   creating, from the shape information, a second line group substantially parallel with the pattern edge;
   specifying areas defined by said first line group and said second line group as a lattice group including irradiation positions of a charged particle beam;
   deciding an order to irradiate the areas with the charged particle beam so that the lattice group is sequentially scanned in a direction of the first or second line group; and
   scanning the subject with the charged particle beam in accordance with the irradiation order to obtain a profile indicating contrast between the pattern edge and adjacent to the pattern edge.

2. The charged particle beam irradiation method according to claim 1, wherein
   creating said first line group includes:
   dividing the pattern edge into a finite number of segments; and
   creating straight lines passing through a boundary between said segments and perpendicular to the pattern edge, and specifying said lattice group includes:
   setting a distance to scan with the charged particle beam as a scanning distance;
   setting a zonal area whose width corresponds to the scanning distance to a direction along the pattern edge; and
   said second line group is created by dividing the zonal area into a finite number of areas in a direction perpendicular to the pattern edge.

3. The charged particle beam irradiation method according to claim 2, wherein
   a length of the segment can be locally adjusted depending on an arbitrary size of pixels constituting an image of the pattern obtained by the irradiation of the charged particle beam.

4. The charged particle beam irradiation method according to claim 1, wherein
   creating said second line group includes:
   obtaining an image of the pattern and calculating a potential function of the image thereof; and
   creating an equipotential curve connecting equivalent values of the potential function to specify the equipotential curve as said second line group, and
   said first line group is created by drawing a line group substantially perpendicular to the equipotential curve.

5. The charged particle beam irradiation method according to claim 4, wherein
   calculating the potential function includes:
   expressing the image with a complex plane $z=x+iy$, and defining a potential function $V(z)$ on the basis of a grayscale value of a pixel located at a point on the complex plane so that the potential function $V(z)$ becomes a regular function; and
   said first line group is created by obtaining a function $W(z)$ derived from a relation of Cauchy-Riemann with respect to the potential function $V(z)$ and calculating a curve group on the z plane where W=constant number.

6. The charged particle beam irradiation method according to claim 1, wherein
   the shape information of the pattern edge is created on the basis of design information or CAD information of a product manufactured in a manufacturing process including drawing of the pattern.

7. The charged particle beam irradiation method according to claim 1, wherein
the charged particle beam includes at least one of an electron beam and an ion beam.

8. A method of manufacturing a semiconductor device comprising a charged particle beam irradiation method including:
obtaining shape information of an edge of a pattern to be inspected that is formed on a subject;
creating, from the shape information, a first line group substantially perpendicular to the pattern edge;
creating, from the shape information, a second line group substantially parallel with the pattern edge;
specifying areas defined by said first line group and said second line group as a lattice group including irradiation positions of a charged particle beam
deciding an order to irradiate the areas with the charged particle beam so that the lattice group is sequentially scanned in a direction of the first or second line group; and
scanning the subject with the charged particle beam in accordance with the irradiation order to obtain a profile indicating contrast between the pattern edge and adjacent to the pattern edge.

9. A charged particle beam apparatus comprising: a charged particle beam source section which generates a charged particle beam and irradiates a subject with the charged particle beam, a pattern to be inspected being formed on the subject;
a deflector which deflects the charged particle beam to scan the subject therewith; and obtain an image having a scanning plane expressed in a first coordinate system;
a scanning image converter which converts said first coordinate system into a second coordinate system:
a calculator which creates in said second coordinate system a first line group substantially perpendicular to the pattern edge and a second line group substantially parallel with the pattern edge from shape information of an edge of the pattern to specify one of directions of the first and second line groups as a scanning direction and which specifies areas defined by said first line group and said second line group as a lattice group including irradiation.

10. The charged particle beam apparatus according to claim 9, wherein
the calculator creates said first line group by dividing the pattern edge into a finite number of segments and creating straight lines passing through a boundary between said segments and perpendicular to the pattern edge, specifies said lattice groups by setting a distance to scan with the charged particle beam as a scanning distance and setting a zonal area whose width corresponds to the scanning distance to a direction along the pattern edge, and divides the zonal area into a finite number of areas in a direction perpendicular to the pattern edge to create said second line group.

11. The charged particle beam apparatus according to claim 10, wherein
a length of the segment can be locally adjusted depending on an arbitrary size of pixels constituting an image of the pattern obtained by the irradiation of the charged particle beam.

12. The charged particle beam apparatus according to claim 9, wherein
the calculator receives an input of the image of the pattern to calculate potential function of the image thereof and creates an equipotential curve connecting equivalent values of the potential function to specify the equipotential curve as said second fine group, and further creates a line group substantially perpendicular to the equipotential curve to create said first line group.

13. The charged particle beam apparatus according to claim 12, wherein
the calculator calculates the potential function by expressing the image with a complex plane $z=x+iy$ and defining a potential function $V(z)$ on the basis of a grayscale value of a pixel located at a point on the complex plane so that the potential function $V(z)$ becomes a regular function, and further creates said first line group by obtaining a function $W(z)$ derived from a relation of Cauchy-Riemann with respect to the potential function $V(z)$ and calculating a curve group on the z plane where W=constant number.

14. The charged particle beam apparatus according to claim 9, wherein
the shape information of the pattern edge is created on the basis of design information or CAD information of a product manufactured in a manufacturing process including drawing of the pattern.

15. The charged particle beam apparatus according to claim 9, wherein
the charged particle beam includes at least one of an electron beam and an ion beam.

* * * * *